United States Patent
Fedorov et al.

(10) Patent No.: US 12,194,060 B2
(45) Date of Patent: Jan. 14, 2025

(54) METHOD FOR THE PRODUCTION OF IODINATED PROTEINS WITH A DETERMINATED IODINE CONTENT

(71) Applicant: "I2LIFE" LIMITED LIABILITY COMPANY ("I2LIFE" LLC), Moscow (RU)

(72) Inventors: Aleksandr Anatolievich Fedorov, R/p Krasny Yar (RU); Feliks Chimenovich Diu, Moskovsky (RU); Irina Nikolaevna Liublinskaia, Borovsk (RU); Stanislav Lyudvigovich Liublinskii, Borovsk (RU)

(73) Assignee: "I2LIFE" LIMITED LIABILITY COMPANY ("I2LIFE" LLO), Moscow (RU)

( * ) Notice: Subject to any disclaimer, the term of this patent is extended or adjusted under 35 U.S.C. 154(b) by 543 days.

(21) Appl. No.: 17/618,668

(22) PCT Filed: Jun. 12, 2020

(86) PCT No.: PCT/RU2020/050119
§ 371 (c)(1),
(2) Date: Dec. 13, 2021

(87) PCT Pub. No.: WO2020/251412
PCT Pub. Date: Dec. 17, 2020

(65) Prior Publication Data
US 2022/0241323 A1 Aug. 4, 2022

(30) Foreign Application Priority Data
Jun. 14, 2019 (RU) .......................... RU2019118567
Jun. 11, 2020 (RU) .......................... RU2020119550

(51) Int. Cl.
| | | |
|---|---|---|
| A61K 33/18 | (2006.01) | |
| A23J 3/08 | (2006.01) | |
| A23J 3/16 | (2006.01) | |
| A23J 3/20 | (2006.01) | |
| A23K 20/147 | (2016.01) | |
| A23L 33/00 | (2016.01) | |
| A23L 33/18 | (2016.01) | |
| A23L 33/185 | (2016.01) | |
| A23L 33/19 | (2016.01) | |
| A23L 33/195 | (2016.01) | |
| A61K 9/08 | (2006.01) | |
| A61K 47/42 | (2017.01) | |
| C12P 21/02 | (2006.01) | |

(52) U.S. Cl.
CPC ................. *A61K 33/18* (2013.01); *A23J 3/08* (2013.01); *A23J 3/16* (2013.01); *A23J 3/20* (2013.01); *A23K 20/147* (2016.05); *A23L 33/18* (2016.08); *A23L 33/185* (2016.08); *A23L 33/19* (2016.08); *A23L 33/195* (2016.08); *A23L 33/40* (2016.08); *A61K 9/08* (2013.01); *A61K 47/42* (2013.01); *C12P 21/02* (2013.01); *A23V 2002/00* (2013.01)

(58) Field of Classification Search
CPC .......... A61K 33/18; A61K 9/08; A61K 47/42; A61K 38/01; A23J 3/08; A23J 3/16; A23J 3/20; A23J 3/346; A23J 3/347; A23J 3/343; A23K 20/147; A23L 33/18; A23L 33/185; A23L 33/19; A23L 33/195; A23L 33/40; C12P 21/02; A23V 2002/00
See application file for complete search history.

(56) References Cited

FOREIGN PATENT DOCUMENTS

| | | |
|---|---|---|
| EA | 007301 | 8/2006 |
| RU | 2156132 | 9/2000 |
| RU | 2212155 | 9/2003 |

OTHER PUBLICATIONS

Hamlin J. L. et al., "Monoiodoinsuline: Preparation, Purification, and Characterization of a Biologically Active Derivative Substituted Predominantly on Tyrosine A14", The JBC, Jan. 1974, vol. 249 (1), pp. 21-32. (Year: 1974).*
RU 2212155 C1—"Method of obtaining biologically active food additive", English translation, total pp. 1-4. (Year: 2003).*
International Search Report for PCT/RU2020/050119, mailed Jun. 3, 2021, 3 pages.
Written Opinion of the ISA for PCT/RU2020/050119, mailed Jun. 3, 2021, 4 pages.

* cited by examiner

*Primary Examiner* — Satyendra K Singh
(74) *Attorney, Agent, or Firm* — Nixon & Vanderhye PC

(57) ABSTRACT

The present disclosure relates to the method for the production of iodinated proteins to be used as biologically active substances and can be used for preventing and treating of the iodine deficiency conditions in humans and animals, in particular, when producing food products, biologically active food supplements, medicinal agents and veterinary preparations and foodstuffs. To this end, a method for the production of iodinated proteins and/or their hydrolyzates is proposed, comprising fermentation of the source protein raw material with an inorganic iodine aqueous solution by introducing therein a buffer mixture of reagents with a reaction mixture of enzymes immobilized on semipermeable membranes or on inert supports. The invention provides for the production of proteins with a determinated iodinated tyrosine amino acid residues content.

4 Claims, No Drawings

METHOD FOR THE PRODUCTION OF IODINATED PROTEINS WITH A DETERMINATED IODINE CONTENT

This application is the U.S. national phase of International Application No. PCT/RU2020/050119 filed 12 Jun. 2020, which designated the U.S. and claims priority to RU patent application No. 2019118567 filed 14 Jun. 2019, and RU patent application No. 2020119550 filed 11 Jun. 2020, the entire contents of each of which are hereby incorporated by reference.

FIELD OF THE INVENTION

The present disclosure relates to the field of medicine, more specifically, to a method for manufacturing the iodinated proteins to be used as biologically active substances and can be used for preventing and treating the iodine deficiency conditions in humans and animals, in particular, when producing food products, biologically active food supplements, enteral and parenteral nutrition items, medicinal agents and veterinary preparations and foodstuffs.

BACKGROUND

The prior art discloses a method for the production of biologically active food supplement that includes iodination of the source protein raw material by its mixing with an inorganic iodine aqueous solution in the selected inorganic iodine/crude protein proportion of (2-40):1, fermentation of the initial whey proteins/inorganic iodine aqueous solution mixture by introduction of a reagents buffer solution (a mixture of NaCl mineral salts and Na and K phosphates with the reaction mixture of enzymes immobilized on semipermeable membranes or on inert supports), wherein the fermentation process is carried out while continuously monitoring the solution iodine content, the iodinated proteins aqueous solution is purified of the macro- and micro impurities, including of inorganic iodine, using the processes of macro filtration, micro filtration and ultra filtration with the subsequent diafiltration of the iodinated proteins aqueous solution in an ultra filtration plant, with the obtained iodinated proteins solution being subjected to sterilizing micro filtration with the subsequent sublimation drying to obtain the finished powdered product. (see Patent RU No. 2212155, IPC A 23 L 1/30, 20.09.2003).

Nevertheless, the known method, in its use, is characterized by the following shortcomings:
  it does not provide for the production of iodinated proteins containing amino acids in certain proportions, namely, monoiodotyrosines, diiodotyrosines and triiodotyrosines,
  it does not provide for the production of a finished powdered product with a high content of a determinated covalently bound iodine,
  it does not allow obtaining a finished powdered product with the necessary characteristics of the organic iodine distribution and accumulation in the human and animal bodies,
  it does not allow obtaining a finished powdered product with the necessary characteristics of the organic iodine distribution and accumulation in the liver, tissues and organs with the participation of deiodinases,
  it does not provide for the sufficient industrial-scale production of iodinated milk whey proteins,
  it cannot provide for the production of iodinated milk whey proteins with hypoallergenic properties.

DISCLOSURE OF THE INVENTION

The object of the invention is to develop a method for the iodinated proteins production to use them as biologically active substances.

The technical result consists in providing for the production of iodinated proteins (and/or iodinated protein hydrolyzate) with the optimal content of iodinated amino acid residues—monoiodotyrosines, diiodotyrosines and triiodotyrosines, providing for the production of a finished powdered product with high determinated covalently bound iodine content and providing for the production of a finished powdered product with the necessary characteristics of the organic iodine distribution and accumulation in humans and in animals, with the participation of deiodinases in liver, tissues and organs. Additionally, the technical result consists in providing for the industrial-scale production of iodinated proteins (and/or hydrolyzates), in particular, iodinated milk whey proteins, including those with hypoallergenic properties.

The technical result is achieved owing to the fact that a method has been proposed for the production of iodinated proteins and/or protein hydrolyzate, comprising the following:
  implementation of the source protein raw material iodination process by mixing the source protein raw material with an inorganic iodine aqueous solution in the selected inorganic iodine/source protein raw material proportion of (2-40):1,
  fermenting the source protein raw material with an inorganic iodine aqueous solution by introducing a reagents buffer solution therein—a mixture of NaCl mineral salts and Na and K phosphates with the reaction mixture of enzymes immobilized on semipermeable membranes or on inert supports,
  wherein the fermentation process is carried out while continuously monitoring the solution iodine content and the iodinated proteins aqueous solution is purified of the macro- and micro impurities, including of inorganic iodine, using the processes of macro filtration, micro filtration and ultra filtration with the subsequent diafiltration of the iodinated proteins' and/or protein hydrolyzate aqueous solution in an ultra filtration plant,
  the obtained iodinated proteins' and/or protein hydrolyzate solution is subjected to sterilizing micro filtration and then
  to the sublimation' or spray drying to obtain a finished powdered product,
  wherein the iodination process for the source protein raw material when mixed with an inorganic iodine aqueous solution is carried out at a temperature of 20° C.-40° C. by introducing a buffer reagent mixture therein, the NaCl based mixture of mineral salts comprising 14-18% wt of sodium phosphate and 22-28% wt of potassium orthophosphate, with the used enzymes reaction mixture parent solution stability of pH=6-8, the enzymes reaction mixture being a mixture based on lactoperoxidase comprising 16-24% wt of horseradish peroxidase and 14-21% wt of catalase,
  wherein the ultra filtration of the iodinated proteins' and/or protein hydrolyzate aqueous solution in the ultra filtration unit is carried out in a tangential flow-through mode using the membrane modules with a cutoff limit of 300-800 Da at pH 6.0-8.0.

In particular embodiments of the invention, proteins of animal, plant and/or microbial origin and/or a hydrolyzate thereof are used as the source protein raw material.

In some embodiments of the invention, α-lactalbumin, β-lactoglobulin, serum albumin, lactoferrin, immunoglobulins and/or a mixture of the mentioned proteins and/or a hydrolyzate of the mentioned proteins are used as the source protein raw material.

In some particular embodiments of the invention, the content of tyrosine residues in the hydrolyzate amounts to 2-5% wt.

As a result of the method implementation, iodinated proteins and/or protein hydrolyzate are obtained, which constitute a finished powdered product with the determinated (i.e., unambiguously predetermined, in strictly defined positions and amount) covalently bound iodine content of 0.5-4.0% wt in the form of iodinated tyrosine residues—monoiodotyrosine in the amount of 55.0-75.0% wt, diiodotyrosine in the amount of 24.0-43.5% wt and triiodotyrosine in the amount of 1.0-1.5% wt.

Such iodinated proteins and/or protein hydrolysates can be used for the prevention and/or treatment of the iodine deficiency conditions in humans and animals.

The iodinated proteins and/or protein hydrolysates according to the invention can be used for the production of food products, biologically active food supplements, enteral and parenteral nutrition items, medicinal agents, veterinary preparations and foodstuffs for the prevention and/or treatment of the iodine deficiency conditions in humans and animals.

The method is effected as follows. The process of the source protein raw material iodination is carried out by mixing it with an inorganic iodine aqueous solution, in the selected inorganic iodine solution/crude protein proportion of (2-40):1. When carrying out the iodination process, proteins of animal, plant and microbial origin and/or hydrolysates thereof can be used as the source protein raw material. During the iodination process, in particular embodiments of the invention whey proteins (and/or their hydrolysates) are used as the source protein raw material; in some particular embodiments of the invention α-lactalbumin, β-lactoglobulin, serum albumin, lactoferrin or immune globulins and/or a mixture of all of the mentioned proteins, and/or hydrolysates of the mentioned proteins with the content of the naturally occurring tyrosines in the hydralizates in the amount of 2-5% wt are used. That said, mammalian proteins (including those of humans) are preferably used as the proteins of animal origin (or hydrolysates thereof); in particular, human, bovine, caprine etc. milk whey proteins can be used.

The iodination of the source proteins when they are mixed with an inorganic iodine aqueous solution is carried out at a temperature of 20° C.-40° C. by introducing a buffer reagent mixture therein, the NaCl based mixture of mineral salts comprising 14-18% wt of sodium phosphate and 22-28% wt of potassium orthophosphate, with the used enzymes (including those immobilized on semipermeable membranes or on inert supports) reaction mixture parent solution stability of pH=6-8. Moreover, a mixture based on lactoperoxidase comprising 16-24% wt of horseradish peroxidase and 14-21% wt of catalase is used as the enzymes reaction mixture parent solution, and the fermentation process is carried out while continuously monitoring the solution iodine content.

An iodinated proteins aqueous solution is purified from macro impurities and micro impurities, including inorganic iodine, using the processes of macro filtration, micro filtration and ultra filtration, with the subsequent diafiltration of the iodinated proteins aqueous solution in an ultra filtration unit in a tangential flow-through mode using the membrane modules with a cutoff limit of 300-800 Da at pH 6.0-8.0.

The obtained iodinated proteins (and/or hydrolyzate) solution is subjected to sterilizing micro filtration and then to the sublimation' or spray drying to obtain a finished powdered product with the determinated covalently bound iodine content of 0.5-4.0% wt in the form of the mixture of the iodinated amino acids (iodinated tyrosine residues) contained in the iodinated proteins—monoiodotyrosines in the amount of 55.0-75.0% wt, diiodotyrosines in the amount of 24.0-43.5% wt and triiodotyrosines in the amount of 1.0-1.5% wt.

Among the essential features characterizing the proposed method of the iodinated proteins (and/or protein hydrolysates) production (in particular, the production of the iodinated milk whey proteins, to be used as biologically active substances (or as parts of compositions)), the distinctive ones are as follows:

use in the preferred embodiments of the invention as a source protein raw material when performing the process of α-lactalbumin, β-lactoglobulin, serum albumin, lactoferrin or immune globulins iodination, or as a mixture of all of the mentioned proteins or hydrolysates of the mentioned proteins, with the content of naturally occurring tyrosine residues (as part of peptides) in the hydrolysates in the amount of 2-5% wt, the iodination of the source proteins (hydrolysates) when they are mixed with an inorganic iodine aqueous solution is carried out at a temperature of 20° C.-40° C. by introducing a buffer reagent mixture therein, the NaCl based mixture of mineral salts comprising 14-18% wt of sodium phosphate and 22-28% wt of potassium orthophosphate (NaCl—the balance) with the used enzymes reaction mixture parent solution stability of pH=6-8, the said enzymes reaction mixture being a mixture based on lactoperoxidase containing 16-24% wt of horseradish peroxidase and 14-21% wt of catalase (lactoperoxidase—the balance), ultra filtration of the iodinated proteins (hydrolysates) aqueous solution in an ultra filtration unit in a tangential flow-through mode using the membrane modules with a cutoff limit of 300-800 Da at pH 6.0-8.0, obtaining, after the ultra filtration and the subsequent sublimation' or spray drying, of a finished powdered product with the determinated covalently bound iodine content of 0.5-4.0% wt in the form of the iodinated amino acids (iodinated tyrosine residues) contained in the iodinated proteins (peptides)—monoiodotyrosines in the amount of 55.0-75.0% wt, diiodotyrosines in the amount of 24.0-43.5% wt and triiodotyrosines in the amount of 1.0-1.5% wt, use of the proteins of animal, plant and microbial origin (and/or hydrolysates thereof) as the source protein raw material in the iodination process.

The experimental studies of the proposed method for the iodinated proteins production for their use as biologically active substances have shown the high efficiency thereof. The method for the iodinated proteins production provides for the production of iodinated proteins with the optimal amino acids (monoiodotyrosines, diiodotyrosines and triiodotyrosines) content, provides for the production of a finished powdered product with a high determinated covalently bound iodine content and provides for the production of a finished powdered product with the necessary characteristics of the organic iodine distribution and accumulation in the human and animal body. Additionally, the proposed method provides for the production of a finished powdered product with the necessary characteristics of the organic iodine distribution and accumulation with the participation of deiodinases in the liver, in tissues and organs, also providing for the industrial-scale production of iodinated proteins, in particular, iodinated milk whey proteins, including those with hypoallergenic properties.

The iodinated proteins and/or protein hydrolysates according to the invention can be used for the prevention and/or treatment of the iodine deficiency conditions in humans and animals. To this purpose, they can be used both independently as biologically active substances, and as part of the food products, biologically active food supplements, enteral and parenteral nutrition means, medicinal agents and veterinary drugs and foodstuffs (the list is not exclusive).

To this end, the iodinated proteins and/or protein hydrolysates according to the invention are incorporated into the said compositions in pharmaceutically effective amounts, i.e., in the amounts providing for the achievement of the desired result. The iodinated proteins and/or protein hydrolysates according to the invention can be included into a composition together with the commonly used non-toxic pharmaceutically acceptable carriers and/or excipients well known to those skilled in the art and suitable for the preparation of solutions, tablets, pills, capsules, dragees, emulsions, suspensions and any other dosage forms. The dosage forms of the present invention are prepared under the standard procedures well known to those skilled in the art.

The implementation of the proposed method for the manufacture of iodinated proteins, in particular, iodinated milk whey proteins, for their use as biologically active substances (or in compositions) is illustrated by the following practical examples.

EXAMPLE 1

A source protein in the form of α-lactalbumin was iodinated by mixing it with an inorganic iodine aqueous solution in the selected inorganic iodine solution/crude protein proportion of 2:1.

The source α-lactalbumin whey protein was iodinated when mixed with an inorganic iodine aqueous solution at the temperature of 30° C. by introducing a buffer reagent mixture, the NaCl based mixture of mineral salts comprising 18% wt of sodium phosphate and 22% wt of potassium orthophosphate, with the used enzymes (immobilized on semipermeable membranes) reaction mixture parent solution stability of pH=6. Moreover, a mixture based on lactoperoxidase containing 16% wt of horseradish peroxidase and 21% wt of catalase was used as the enzymes reaction mixture parent solution, and the fermentation process was carried out while continuously monitoring the solution iodine content.

The iodinated proteins aqueous solution was purified from macro- and micro impurities, including from inorganic iodine, using the processes of macro filtration, micro filtration and ultra filtration, with the subsequent diafiltration of the iodinated proteins aqueous solution in an ultra filtration unit in a tangential flow-through mode using the membrane modules with a minimum cutoff limit of 500 Da at pH 8.0.

The obtained iodinated proteins solution was subjected to sterilizing micro filtration and then to the sublimation drying to obtain a finished powdered product with the determinated covalently bound iodine content of 2.5% wt in the form of iodinated amino acid residues contained in iodinated proteins—monoiodotyrosines in the amount of 75.0% wt, diiodotyrosines in the amount of 24.0% wt and triiodotyrosines in the amount of 1.0% wt.

EXAMPLE 2

A source protein in the form of β-lactoglobulin was iodinated by mixing it with an inorganic iodine aqueous solution in the selected inorganic iodine solution/crude protein proportion of 10:1.

The source β-lactalbumin whey protein was iodinated when mixed with an inorganic iodine aqueous solution at the temperature of 20° C. by introducing a buffer reagent mixture, the NaCl based mixture of mineral salts comprising 14% wt of sodium phosphate and 28% wt of potassium orthophosphate, with the used enzymes (immobilized on inert supports) reaction mixture parent solution stability of pH=7. Moreover, a mixture based on lactoperoxidase containing 18% wt of horseradish peroxidase and 19% wt of catalase was used as the enzymes reaction mixture parent solution, and the fermentation process was carried out while continuously monitoring the solution iodine content.

The iodinated proteins aqueous solution was purified from macro- and micro impurities, including from inorganic iodine, using the processes of macro filtration, micro filtration and ultra filtration, with the subsequent diafiltration of the iodinated proteins aqueous solution in an ultra filtration unit in a tangential flow-through mode using the membrane modules with a minimum cutoff limit of 300 Da at pH 7.0.

The obtained iodinated proteins solution was subjected to sterilizing micro filtration and then to the spray drying to obtain a finished powdered product with the determinated covalently bound iodine content of 1.7% wt in the form of iodinated amino acid residues contained in iodinated proteins—monoiodotyrosines in the amount of 55.0% wt, diiodotyrosines in the amount of 43.5% wt and triiodotyrosines in the amount of 1.5% wt.

EXAMPLE 3

A source protein in the form of serum albumin was iodinated by mixing it with an inorganic iodine aqueous solution in the selected inorganic iodine solution/crude protein proportion of 20:1.

The source serum albumin protein was iodinated when mixed with an inorganic iodine aqueous solution at the temperature of 40° C. by introducing a buffer reagent mixture, the NaCl based mixture of mineral salts comprising 15% wt of sodium phosphate and 23% wt of potassium orthophosphate, with the used enzymes (immobilized on inert supports) reaction mixture parent solution stability of pH=8. Moreover, a mixture based on lactoperoxidase containing 24% wt of horseradish peroxidase and 14% wt of catalase was used as the enzymes reaction mixture parent solution, and the fermentation process was carried out while continuously monitoring the solution iodine content.

The iodinated proteins aqueous solution was purified from macro- and micro impurities, including from inorganic iodine, using the processes of macro filtration, micro filtration and ultra filtration, with the subsequent diafiltration of the iodinated proteins aqueous solution in an ultra filtration unit in a tangential flow-through mode using the membrane modules with a minimum cutoff limit of 800 Da at pH 6.0.

The obtained iodinated proteins solution was subjected to sterilizing micro filtration and then to the sublimation drying to obtain a finished powdered product with the determinated covalently bound iodine content of 0.7% wt in the form of iodinated amino acid residues contained in iodinated proteins—monoiodotyrosines in the amount of 65.0% wt, diiodotyrosines in the amount of 34.0% wt and triiodotyrosines in the amount of 1.0% wt.

EXAMPLE 4

A source protein in the form of lactoferrin was iodinated by mixing it with an in organic iodine aqueous solution in the selected inorganic iodine solution/crude protein proportion of 30:1.

The source lactoferrin whey protein was iodinated when mixed with an inorganic iodine aqueous solution at the temperature of 25° C. by introducing a buffer reagent mixture, the NaCl based mixture of mineral salts comprising 17% wt of sodium phosphate and 26% wt of potassium orthophosphate, with the used enzymes (immobilized on semipermeable membranes) reaction mixture parent solution stability of pH=8. Moreover, a mixture based on lactoperoxidase containing 22% wt of horseradish peroxidase and 17% wt of catalase was used as the enzymes reaction mixture parent solution, and the fermentation process was carried out while continuously monitoring the solution iodine content.

The iodinated proteins aqueous solution was purified from macro- and micro impurities, including from inorganic iodine, using the processes of macro filtration, micro filtration and ultra filtration, with the subsequent diafiltration of the iodinated proteins aqueous solution in an ultra filtration unit in a tangential flow-through mode using the membrane modules with a minimum cutoff limit of 600 Da at pH 7.0.

The obtained iodinated proteins solution was subjected to sterilizing micro filtration and then to the sublimation drying to obtain a finished powdered product with the determinated covalently bound iodine content of 0.5% wt in the form of iodinated amino acid residues contained in iodinated proteins—monoiodotyrosines in the amount of 60.0% wt, diiodotyrosines in the amount of 38.5% wt and triiodotyrosines in the amount of 1.5% wt.

EXAMPLE 5

A source protein in the form of immune serum globulins was iodinated by mixing it with an inorganic iodine aqueous solution in the selected inorganic iodine solution/crude protein proportion of 40:1.

The source immune serum globulins protein was iodinated when mixed with an inorganic iodine aqueous solution at the temperature of 30° C. by introducing a buffer reagent mixture, the NaCl based mixture of mineral salts comprising 16% wt of sodium phosphate and 27% wt of potassium orthophosphate, with the used enzymes (immobilized on semipermeable membranes) reaction mixture parent solution stability of pH=7. Moreover, a mixture based on lactoperoxidase containing 21% wt of horseradish peroxidase and 18% wt of catalase was used as the enzymes reaction mixture parent solution, and the fermentation process was carried out while continuously monitoring the solution iodine content.

The iodinated proteins aqueous solution was purified from macro- and micro impurities, including from inorganic iodine, using the processes of macro filtration, micro filtration and ultra filtration, with the subsequent diafiltration of the iodinated proteins aqueous solution in an ultra filtration unit in a tangential flow-through mode using the membrane modules with a minimum cutoff limit of 400 Da at pH 8.0.

The obtained iodinated proteins solution was subjected to sterilizing micro filtration and then to the spray drying to obtain a finished powdered product with the determinated covalently bound iodine content of 1.2% wt in the form of iodinated amino acid residues contained in iodinated proteins—monoiodotyrosines in the amount of 70.0% wt, diiodotyrosines in the amount of 28.5% wt and triiodotyrosines in the amount of 1.5% wt.

EXAMPLE 6

A source protein in the form of α-lactalbumin, β-lactoglobulin, serum albumin, lactoferrin and immune globulins mixture was iodinated by mixing it with an inorganic iodine aqueous solution in the selected inorganic iodine solution/ crude protein raw material proportion of 30:1.

The source protein raw material in the form of α-lactalbumin, β-lactoglobulin, serum albumin, lactoferrin and immune globulins mixture was iodinated when mixed with an inorganic iodine aqueous solution at the temperature of 35° C. by introducing a buffer reagent mixture, the NaCl based mixture of mineral salts comprising 18% wt of sodium phosphate and 24% wt of potassium orthophosphate, with the used enzymes (immobilized on inert supports) reaction mixture parent solution stability of pH=6. Moreover, a mixture based on lactoperoxidase containing 19% wt of horseradish peroxidase and 16% wt of catalase was used as the enzymes reaction mixture parent solution, and the fermentation process was carried out while continuously monitoring the solution iodine content.

The iodinated proteins aqueous solution was purified from macro- and micro impurities, including from inorganic iodine, using the processes of macro filtration, micro filtration and ultra filtration, with the subsequent diafiltration of the iodinated proteins aqueous solution in an ultra filtration unit in a tangential flow-through mode using the membrane modules with a minimum cutoff limit of 700 Da at pH 6.0.

The obtained iodinated proteins solution was subjected to sterilizing micro filtration and then to the sublimation drying to obtain a finished powdered product with the determinated covalently bound iodine content of 2.0% wt in the form of iodinated amino acid residues contained in iodinated proteins—monoiodotyrosines in the amount of 68.0% wt, diiodotyrosines in the amount of 31.0% wt and triiodotyrosines in the amount of 1.0% wt.

EXAMPLE 7

A source protein raw material in the form of α-lactalbumin hydrolyzate with the naturally occurring tyrosines content of 5% wt was iodinated by its mixing with an inorganic iodine aqueous solution in the selected inorganic iodine/ source protein raw material proportion of 25:1.

The source protein raw material in the form of α-lactalbumin hydrolyzate was iodinated when mixed with an inorganic iodine aqueous solution at the temperature of 20° C. by introducing a buffer reagent mixture, the NaCl based mixture of mineral salts comprising 15% wt of sodium phosphate and 27% wt of potassium orthophosphate, with the used enzymes (immobilized on semipermeable membranes) reaction mixture parent solution stability of pH=7. Moreover, a mixture based on lactoperoxidase containing 17% wt of horseradish peroxidase and 20% wt of catalase was used as the enzymes reaction mixture parent solution, and the fermentation process was carried out while continuously monitoring the solution iodine content.

The iodinated peptides aqueous solution was purified from macro- and micro impurities, including from inorganic iodine, using the processes of macro filtration, micro filtration and ultra filtration, with the subsequent diafiltration of the iodinated proteins aqueous solution in an ultra filtration unit in a tangential flow-through mode using the membrane modules with a minimum cutoff limit of 300 Da at pH 7.0.

The obtained iodinated peptides solution was subjected to sterilizing micro filtration and then to the spray drying to obtain a finished powdered product with the determinated covalently bound iodine content of 4.0% wt in the form of iodinated amino acid residues contained in iodinated peptides—monoiodotyrosines in the amount of 70.0% wt, diiodotyrosines in the amount of 29.0% wt and triiodotyrosines in the amount of 1.0% wt.

EXAMPLE 8

The source protein raw material in the form of β-lactoglobulin hydrolyzate with the naturally occurring tyrosines content of 3.5% wt was iodinated by its mixing with an inorganic iodine aqueous solution in the selected inorganic iodine/source protein raw material proportion of 35:1.

The source protein raw material in the form of β-lactoglobulin hydrolyzate was iodinated when mixed with an inorganic iodine aqueous solution at the temperature of 40° C. by introducing a buffer reagent mixture, the NaCl based mixture of mineral salts comprising 14% wt of sodium phosphate and 25% wt of potassium orthophosphate, with the used enzymes (immobilized on inert supports) reaction mixture parent solution stability of pH=7. Moreover, a mixture based on lactoperoxidase containing 20% wt of horseradish peroxidase and 21% wt of catalase was used as the enzymes reaction mixture parent solution, and the fermentation process was carried out while continuously monitoring the solution iodine content.

The iodinated peptides aqueous solution was purified from macro- and micro impurities, including from inorganic iodine, using the processes of macro filtration, micro filtration and ultra filtration, with the subsequent diafiltration of the iodinated proteins aqueous solution in an ultra filtration unit in a tangential flow-through mode using the membrane modules with a minimum cutoff limit of 800 Da at pH 8.0.

The obtained iodinated peptides solution was subjected to sterilizing micro filtration and then to the sublimation drying to obtain a finished powdered product with the determinated covalently bound iodine content of 3.1% wt in the form of iodinated amino acid residues contained in iodinated peptides—monoiodotyrosines in the amount of 65.0% wt, diiodotyrosines in the amount of 33.5% wt and triiodotyrosines in the amount of 1.5% wt.

EXAMPLE 9

A source protein raw material in the form of serum albumin hydrolyzate with the naturally occurring tyrosines content of 2% wt was iodinated by its mixing with an inorganic iodine aqueous solution in the selected inorganic iodine/source protein raw material proportion of 15:1.

The source serum albumin hydrolyzate was iodinated when mixed with an inorganic iodine aqueous solution at the temperature of 30° C. by introducing a buffer reagent mixture, the NaCl based mixture of mineral salts comprising 16% wt of sodium phosphate and 22% wt of potassium orthophosphate, with the used enzymes (immobilized on semipermeable membranes) reaction mixture parent solution stability of pH=8. Moreover, a mixture based on lactoperoxidase containing 24% wt of horseradish peroxidase and 18% wt of catalase was used as the enzymes reaction mixture parent solution, and the fermentation process was carried out while continuously monitoring the solution iodine content.

The iodinated peptides aqueous solution was purified from macro- and micro impurities, including from inorganic iodine, using the processes of macro filtration, micro filtration and ultra filtration, with the subsequent diafiltration of the iodinated proteins aqueous solution in an ultra filtration unit in a tangential flow-through mode using the membrane modules with a minimum cutoff limit of 400 Da at pH 6.0.

The obtained iodinated peptides solution was subjected to sterilizing micro filtration and then to the sublimation drying to obtain a finished powdered product with the determinated covalently bound iodine content of 1.2% wt in the form of iodinated amino acid residues contained in iodinated peptides—monoiodotyrosines in the amount of 75.0% wt, diiodotyrosines in the amount of 24.0% wt and triiodotyrosines in the amount of 1.0% wt.

EXAMPLE 10

A source protein raw material in the form of lactoferrin hydrolyzate with the naturally occurring tyrosines content of 3% wt was iodinated by its mixing with an inorganic iodine aqueous solution in the selected inorganic iodine/source protein raw material proportion of 20:1.

The source lactoferrin hydrolyzate was iodinated when mixed with an inorganic iodine aqueous solution at the temperature of 20° C. by introducing a buffer reagent mixture, the NaCl based mixture of mineral salts comprising 18% wt of sodium phosphate and 20% wt of potassium orthophosphate, with the used enzymes (immobilized on semipermeable membranes) reaction mixture parent solution stability of pH=6. Moreover, a mixture based on lactoperoxidase containing 23% wt of horseradish peroxidase and 14% wt of catalase was used as the enzymes reaction mixture parent solution, and the fermentation process was carried out while continuously monitoring the solution iodine content.

The iodinated peptides aqueous solution was purified from macro- and micro impurities, including from inorganic iodine, using the processes of macro filtration, micro filtration and ultra filtration, with the subsequent diafiltration of the iodinated peptides aqueous solution in an ultra filtration unit in a tangential flow-through mode using the membrane modules with a minimum cutoff limit of 500 Da at pH 8.0.

The obtained iodinated peptides solution was subjected to sterilizing micro filtration and then to the spray drying to obtain a finished powdered product with the determinated covalently bound iodine content of 1.0% wt in the form of iodinated amino acid residues contained in iodinated peptides—monoiodotyrosines in the amount of 60.0% wt, diiodotyrosines in the amount of 39.0% wt and triiodotyrosines in the amount of 1.0% wt.

EXAMPLE 11

A source protein raw material in the form of hydrolyzates of the α-lactalbumin, β-lactoglobulin, serum albumin, lactoferrin and immune globulins mixture with the naturally occurring tyrosines content of 5% wt was iodinated by its mixing with an inorganic iodine aqueous solution with the selected inorganic iodine/source protein raw material proportion of 40:1.

The source protein raw material in the form of hydrolyzates of the α-lactalbumin, β-lactoglobulin, serum albumin, lactoferrin and immune globulins mixture was iodinated when mixed with an inorganic iodine aqueous solution at the temperature of 40° C. by introducing a buffer reagent mixture, the NaCl based mixture of mineral salts comprising 17% wt of sodium phosphate and 28% wt of potassium orthophosphate, with the used enzymes (immobilized on inert supports) reaction mixture parent solution stability of pH=7. Moreover, a mixture based on lactoperoxidase containing 18% wt of horseradish peroxidase and 21% wt of catalase was used as the enzymes reaction mixture parent solution, and the fermentation process was carried out while continuously monitoring the solution iodine content.

The iodinated peptides aqueous solution was purified from macro- and micro impurities, including from inorganic iodine, using the processes of macro filtration, micro filtration and ultra filtration, with the subsequent diafiltration of the iodinated peptides aqueous solution in an ultra filtration unit in a tangential flow-through mode using the membrane modules with a minimum cutoff limit of 800 Da at pH 7.0.

The obtained iodinated peptides solution was subjected to sterilizing micro filtration and then to the spray drying to obtain a finished powdered product with the determinated covalently bound iodine content of 3.0% wt in the form of iodinated amino acid residues contained in iodinated peptides—monoiodotyrosines in the amount of 68.0% wt, diiodotyrosines in the amount of 30.5% wt and triiodotyrosines in the amount of 1.5% wt.

EXAMPLE 12

A source protein of an animal origin in the form of bovine serum albumin with the tyrosine content of 2% was iodinated by mixing it with an inorganic iodine aqueous solution in the selected inorganic iodine solution/crude protein proportion of 20:1.

The source protein of an animal origin in the form of bovine serum albumin was iodinated when mixed with an inorganic iodine aqueous solution at the temperature of 30° C. by introducing a buffer reagent mixture, the NaCl based mixture of mineral salts comprising 16% wt of sodium phosphate and 26% wt of potassium orthophosphate, with the used enzymes (immobilized on semipermeable membranes) reaction mixture parent solution stability of pH=8. Moreover, a mixture based on lactoperoxidase containing 22% wt of horseradish peroxidase and 17% wt of catalase was used as the enzymes reaction mixture parent solution, and the fermentation process was carried out while continuously monitoring the solution iodine content.

The iodinated proteins aqueous solution was purified from macro- and micro impurities, including from inorganic iodine, using the processes of macro filtration, micro filtration and ultra filtration, with the subsequent diafiltration of the iodinated proteins aqueous solution in an ultra filtration unit in a tangential flow-through mode using the membrane modules with a minimum cutoff limit of 600 Da at pH 7.0.

The obtained iodinated proteins solution was subjected to sterilizing micro filtration and then to the spray drying to obtain a finished powdered product with the determinated covalently bound iodine content of 0.8% wt in the form of iodinated amino acid residues contained in iodinated proteins—monoiodotyrosines in the amount of 70.0% wt, diiodotyrosines in the amount of 29.0% wt and triiodotyrosines in the amount of 1.0% wt.

EXAMPLE 13

A source protein of an animal origin in the form of soybean protein isolate with the tyrosine content of 2% was iodinated by mixing it with an inorganic iodine aqueous solution in the selected inorganic iodine solution/crude protein proportion of 15:1.

The source protein of an animal origin in the form of soybean protein isolate was iodinated when mixed with an inorganic iodine aqueous solution at the temperature of 20° C. by introducing a buffer reagent mixture, the NaCl based mixture of mineral salts comprising 15% wt of sodium phosphate and 23% wt of potassium orthophosphate, with the used enzymes (immobilized on semipermeable membranes) reaction mixture parent solution stability of pH=7. Moreover, a mixture based on lactoperoxidase containing 24% wt of horseradish peroxidase and 14% wt of catalase was used as the enzymes reaction mixture parent solution, and the fermentation process was carried out while continuously monitoring the solution iodine content.

The iodinated proteins aqueous solution was purified from macro- and micro impurities, including from inorganic iodine, using the processes of macro filtration, micro filtration and ultra filtration, with the subsequent diafiltration of the iodinated proteins aqueous solution in an ultra filtration unit in a tangential flow-through mode using the membrane modules with a minimum cutoff limit of 700 Da at pH 6.0.

The obtained iodinated proteins solution was subjected to sterilizing micro filtration and then to the sublimation drying to obtain a finished powdered product with the determinated covalently bound iodine content of 1.0% wt in the form of iodinated amino acid residues contained in iodinated proteins—monoiodotyrosines in the amount of 60.0% wt, diiodotyrosines in the amount of 39.0% wt and triiodotyrosines in the amount of 1.0% wt.

EXAMPLE 14

A source protein of a microbial origin in the form of baker's yeast isolate with the tyrosine content of 3.5% was iodinated by mixing it with an inorganic iodine aqueous solution in the selected inorganic iodine solution/crude protein proportion of 40:1.

The source protein of a microbial origin in the form of baker's yeast isolate was iodinated when mixed with an inorganic iodine aqueous solution at the temperature of 35° C. by introducing a buffer reagent mixture, the NaCl based mixture of mineral salts comprising 18% wt of sodium phosphate and 28% wt of potassium orthophosphate, with the used enzymes (immobilized on semipermeable membranes) reaction mixture parent solution stability of pH=8. Moreover, a mixture based on lactoperoxidase containing 24% wt of horseradish peroxidase and 14% wt of catalase was used as the enzymes reaction mixture parent solution, and the fermentation process was carried out while continuously monitoring the solution iodine content.

The iodinated proteins aqueous solution was purified from macro- and micro impurities, including from inorganic iodine, using the processes of macro filtration, micro filtration and ultra filtration, with the subsequent diafiltration of the iodinated proteins aqueous solution in an ultra filtration unit in a tangential flow-through mode using the membrane modules with a minimum cutoff limit of 500 Da at pH 7.0.

The obtained iodinated proteins solution was subjected to sterilizing micro filtration and then to the spray drying to obtain a finished powdered product with the determinated covalently bound iodine content in the amount of 1.5% wt in the form of iodinated amino acid residues contained in iodinated proteins—monoiodotyrosines in the amount of 70.0% wt, diiodotyrosines in the amount of 28.5% wt and triiodotyrosines in the amount of 1.5% wt.

Despite the fact that the invention is described with reference to the disclosed embodiments, it should be obvious to those skilled in the art that the particular specified experiments are given only for illustration purposes and they should not be considered as limiting the scope of the invention in any way. Those skilled in the art would appreciate that it is possible to implement different modifications without departing from the spirit and scope of the present invention.

The invention claimed is:

1. A method for the production of iodinated proteins and/or protein hydrolyzate, comprising:
    providing a source protein raw material for the iodination process;
    mixing the source protein raw material with an aqueous inorganic iodine solution in a selected inorganic iodine/source protein raw material proportion of 2:1 to 40:1;
    reacting the source protein raw material with the aqueous inorganic iodine solution by mixing with a buffer solution comprising a mixture of NaCl, Na and K phosphates, and an enzyme reaction mixture comprising enzymes that are immobilized on semipermeable membranes or on inert supports;
    wherein the reaction process is carried out while continuously monitoring the iodine content of the solution, and the aqueous solution comprising the iodinated protein and/or protein hydrolyzate is purified of the macro and micro impurities, including of the inorganic iodine, using the process comprising macrofiltration, microfiltration and ultrafiltration followed by a subsequent diafiltration to obtain purified iodinated protein and/or protein hydrolysate;
    subjecting the purified iodinated protein and/or protein hydrolysate to an sterilizing micro filtration step, followed by sublimation or spray drying to obtain a finished, powdered iodinated product comprising covalently bound iodine content of 0.5-4.0% wt;
    wherein the iodination reaction is carried out at a temperature of 20° C.-40° C. using the buffer solution comprising NaCl, 14-18% wt of sodium phosphate and 22-28% wt of potassium orthophosphate, and the enzymes reaction mixture having solution stability of pH 6-8 comprising 16 24% wt of horseradish peroxidase and 14-21% wt of catalase, with remainder being lactoperoxidase; and
    wherein the ultrafiltration of the aqueous solution comprising iodinated protein and/or protein hydrolyzate in an ultrafiltration unit is carried out in a tangential flow-through mode using membrane modules with a cutoff limit of 300-800 Da at pH 6.0-8.0.

2. The method according to claim 1, wherein α-lactalbumin, β-lactoglobulin, serum albumin, lactoferrin, immunoglobulins and/or a mixture thereof, and/or a hydrolyzate thereof are used as the source protein raw material.

3. The method according to claim 2, wherein a content of tyrosine residues in the hydrolyzate amounts to 2-5% wt.

4. The method according to claim 1, wherein proteins of animal, plant and/or microbial origin, and/or a hydrolyzate thereof are used as the source protein raw material.

* * * * *